United States Patent
Schlotterbeck et al.

(10) Patent No.: US 8,998,485 B2
(45) Date of Patent: Apr. 7, 2015

(54) LASER ANEMOMETRY PROBE SYSTEM AND METHOD EMPLOYING CONTINUOUS COHERENT DETECTION, WITH SINGLE-PARTICLE MODE, CAPABLE OF DETECTING ICE-FORMING CONDITIONS AND OF DETERMINING THE SEVERITY OF ICING

(71) Applicant: Thales, Neuilly/sur/Seine (FR)

(72) Inventors: Jean-Pierre Schlotterbeck, Rochefort-Samson (FR); Xavier LaCondemine, Valence (FR)

(73) Assignee: Thales, Courbevoie (FR)

( * ) Notice: Subject to any disclaimer, the term of this patent is extended or adjusted under 35 U.S.C. 154(b) by 287 days.

(21) Appl. No.: 13/686,584

(22) Filed: Nov. 27, 2012

(65) Prior Publication Data

US 2013/0142214 A1 Jun. 6, 2013

(30) Foreign Application Priority Data

Dec. 2, 2011 (FR) ...................................... 11 03680

(51) Int. Cl.

| | | |
|---|---|---|
| *G01N 25/02* | (2006.01) | |
| *G01J 5/00* | (2006.01) | |
| *G01N 25/04* | (2006.01) | |
| *B64D 15/20* | (2006.01) | |
| *G01P 5/26* | (2006.01) | |
| *G01S 17/58* | (2006.01) | |
| *G01S 17/95* | (2006.01) | |
| *G01S 17/02* | (2006.01) | |
| *G01S 7/491* | (2006.01) | |

(52) U.S. Cl.
CPC ................ *G01N 25/04* (2013.01); *B64D 15/20* (2013.01); *G01P 5/26* (2013.01); *G01S 17/58* (2013.01); *G01S 17/95* (2013.01); *G01S 17/023* (2013.01); *G01S 7/4912* (2013.01)

(58) Field of Classification Search
USPC ............................ 374/17, 16, 130, 120, 141
See application file for complete search history.

(56) References Cited

U.S. PATENT DOCUMENTS

| | | | |
|---|---|---|---|
| 4,483,614 A * | 11/1984 | Rogers ......................... | 356/28.5 |
| 5,641,972 A | 6/1997 | Breda | |
| 2004/0036630 A1 | 2/2004 | Jamieson et al. | |
| 2005/0002435 A1 * | 1/2005 | Hashimoto et al. ............. | 374/43 |
| 2011/0181863 A1 | 7/2011 | Renard et al. | |
| 2013/0162974 A1 * | 6/2013 | Dakin et al. .................... | 356/28 |

FOREIGN PATENT DOCUMENTS

FR 1103680 A 11/1955

OTHER PUBLICATIONS

Institute National De La Propriete Industrielle; Preliminary Search Report; Jul. 12, 2012; Journal Officiel de l'Office europeen des brevets, No. 12/82; France.

* cited by examiner

*Primary Examiner* — Mirellys Jagan
(74) *Attorney, Agent, or Firm* — Michael J. Donohue; Davis Wright Tremaine LLP

(57) ABSTRACT

The laser anemometry probe (LAP) system with continuous coherent detection, with single-particle mode, comprises means (AN) for analyzing the measurement signals of the said probe (LAP) and means (MES_T) for measuring the temperature (T).

The system comprises, furthermore, means (DET_CG) for determining icing conditions when means (DET_GEL) for detecting the presence of a liquid water drop detect the presence of a liquid water drop, and when the said temperature (T) is below the said third threshold (S3).

17 Claims, 3 Drawing Sheets

LASER ANEMOMETRY PROBE SYSTEM AND METHOD EMPLOYING CONTINUOUS COHERENT DETECTION, WITH SINGLE-PARTICLE MODE, CAPABLE OF DETECTING ICE-FORMING CONDITIONS AND OF DETERMINING THE SEVERITY OF ICING

BACKGROUND OF THE INVENTION

1. Field of the Invention

The present invention relates to a laser anemometry probe system employing continuous coherent detection, with single-particle mode, capable of detecting icing conditions and optionally of determining the severity of icing, an aircraft equipped with such a system, and an associated method.

The present invention relates to a laser anemometry probe system employing continuous coherent detection, with single-particle mode, capable of detecting icing conditions and optionally of determining the severity of icing, an aircraft equipped with such a system, and an associated method.

2. Description of the Related Art

It is well known, particularly in the aeronautical field, that certain drops of supercooled water can lead to icing and present a danger to the aeroplane which is not certified under these conditions.

It is well known, particularly in the aeronautical field, that certain drops of supercooled water can lead to icing and present a danger to the aeroplane which is not certified under these conditions.

Protection against icing has given rise to the realization of preventive or corrective devices. Icing conditions occur when the atmosphere in which the aircraft is flying contains supercooled droplets (liquid water at a temperature below the freezing point temperature). The phenomenon of icing can appear on the unprotected protuberant parts of aircraft.

Detection of the icing conditions induced by the presence of supercooled water can aid the pilot in respect of the decision to trigger the de-icing of the aeroplane.

The installation of an icing severity detector, such as vibrating rods, leads to the installation of a further item of equipment, this requiring a hole in the aeroplane skin, extra cost, and additional fuel consumption.

Moreover, the icing severity detector begins to indicate information after the start of icing, which may turn out to be too late, notably if there are points on the aircraft under more severe conditions that those at the detector.

The use of a LiDAR system is known, based on the analysis of the depolarization of the optical signal backscattered by a frozen water particle.

SUMMARY OF THE INVENTION

An aim of the invention is to propose an alternative approach based on a LiDAR system not utilizing the polarization of the backscattered optical signal.

An aim of the invention is to propose an alternative approach based on a LiDAR system not utilizing the polarization of the backscattered optical signal.

There is proposed, according to one aspect of the invention, a laser anemometry probe system employing continuous coherent detection, with single-particle mode, comprising:
 means for analysing the measurement signals of the said probe;
 means for measuring the temperature;

characterized in that it comprises, furthermore:
 first means for comparing a first discrepancy, over a duration of observation of the said measurement signals, between the phase of the signal measured by the said probe and an expected phase, estimated on the basis of values of parameters characteristic of the laser beam emitted by the said probe, corresponding to the transit of a spherical particle, with a first threshold of phase discrepancy;
 second means for comparing a second discrepancy, over the said duration of observation of the said measurement signals, between the amplitude of the signal measured by the said probe and an expected amplitude, estimated as a function of values of parameters characteristic of the laser beam emitted by the said probe, corresponding to the transit of a spherical particle, with a second threshold of amplitude discrepancy;
 third means for comparing the said temperature with a third threshold of temperature;
 means for detecting the presence of a liquid water drop when the said first discrepancy is below the said first threshold and the said second discrepancy is below the said second threshold; and
 means for determining icing conditions when the said means for detecting the presence of a liquid water drop detect the presence of a liquid water drop, and when the said temperature is below the said third threshold.

Such a system makes it possible, at very little extra cost, to detect a risk of icing, on the basis of an already present laser anemometry probe.

The invention applies to a laser anemometry probe, employing coherent detection and with single-particle configuration. In such a system, the signal resulting from the transit of a particle in the beam (of generally Gaussian profile) is characterized by:
 the central frequency, representative of the speed of the particle (optionally modulated continuously if the particle crosses the beam in a zone where the wavefronts are curved);
 the duration, dependent on the size of the particle and the diameter of the beam at the point where the particle crosses it; and
 the amplitude, dependent on the illumination power and the backscattering cross-section of the particle.

The scattering pattern of a particle depends essentially on its size and its geometry (roughness or presence of facets, estimated on the scale of the wavelength of the illuminator).

When the particle is a liquid droplet, the particle is approximately spherical and exhibits a relatively smooth surface state. The backscattering is then very insensitive to the orientation of the particle with respect to the beam (this situation is well described by the Mie theory).

Conversely, when the particle is an ice crystal, the large number of facets produces a complex scattering pattern (large number of narrow lobes) and the backscattering will be very sensitive to the orientation of the particle with respect to the beam.

The signal resulting from the backscattering off a facetted particle such as an ice crystal is distinguished from the signal resulting from the backscattering off an almost spherical particle by the presence of abrupt amplitude and phase variations (to be viewed in relation to the measurement noise and the variations due to the roughness of the particle), corresponding to the consecutive illumination of various facets from different angles.

Icing conditions are detected by the identification of spherical particles (liquid water) at low temperature, typically a temperature of less than 10° C. Indeed the presence of already frozen water does not induce any concretions on the structures of the aircraft and liquid water at higher temperature is not at risk of freezing.

In one embodiment, the said laser anemometry probe delivers a beam with circular polarization, so as to preserve optimal sensitivity, independently of the depolarizing properties of the target (particle) and of the propagation medium.

In one embodiment, the said first threshold (S1) of phase discrepancy lies between 0.1 and 1 radians, to take account of the measurement noise, for example 0.2 radians.

Indeed, this threshold makes it possible to take account of slight discrepancies originating from measurement noise, when drops of liquid water are detected.

According to one embodiment, the said second threshold of amplitude discrepancy is less than 20% of the said expected amplitude.

Likewise, this threshold makes it possible to take account of slight discrepancies originating from measurement noise, when drops of liquid water are detected.

In a previous embodiment, the said third threshold of temperature lies between 5° C. and 15° C., for example 10° C.

Such temperature threshold values are particularly suited to an aeronautical environment. Furthermore the value of 10° C. makes it possible to retain an almost zero error margin.

Furthermore, the system can comprise alerting means for forewarning of a risk of icing, adapted so as to be activated by control means when the said determining means detect icing conditions.

Thus, when the system is on board an aircraft, the pilot and the crew may be alerted. These alerting means may be visual, auditory, the two combined, or other.

In one embodiment, the said control means are adapted for monitoring the evolution of the said temperature after detecting the presence of drops of liquid water.

Thus, when the presence of drops of liquid water is detected, the system monitors the evolution of the temperature so as to easily detect icing conditions if the temperature decreases, until it reaches third threshold. The control means could even, by anticipation, alert of a risk of impending occurrence of icing conditions.

According to one embodiment, the said control means are adapted for monitoring the detection of the presence of drops of liquid water after measurement of the said temperature below the said third threshold.

Thus, when a low temperature is detected, the system monitors the evolution of the detection of presence of drops of liquid water. The control means could even, by anticipation, alert of a risk of impending occurrence of icing conditions.

In one embodiment, the system comprises, furthermore, means for counting the detected drops of liquid water, and means for determining the severity of the icing on the basis of the said counting of the drops of liquid water detected per second.

The official nomenclature defines four levels of icing in ascending order of severity. The severity of the icing depends on the type of aircraft and its means for contending with it. Icing that is considered to be light for an aeroplane of large capacity may be considered to be moderate, or indeed severe for small aircraft. In the report relating to the crash of flight 4184, the NTSB makes the recommendation to the authorities, to the FAA in particular, that an alert system be devised whereby the risks by type of aeroplane should be rendered objective without leaving room for interpretations:

1) Traces: Icing is perceptible. The accumulation rate is slightly greater than the sublimation rate. It is not dangerous even if the deicing or anti-icing systems are not used unless this phenomenon is experienced over an extended period (more than an hour).

2) Light: the accumulation rate can create a problem if the flight extends into this environment (more than an hour). The occasional use of the deicing or anti-icing systems removes, respectively prevents, accumulation. This accumulation does not present any problem if the deicing or anti-icing systems are used.

3) Moderate: the accumulation rate is such that even short exposure can become potentially dangerous. The use of deicing or anti-icing systems or indeed a modification of trajectory are necessary.

4) Severe: the accumulation rate is such that the deicing or anti-icing systems are incapable of reducing or of containing the danger. An immediate trajectory modification is necessary.

According to one embodiment, the system comprising, furthermore, means for estimating the size of a detected liquid water drop, the said determining means are adapted for determining the severity of the icing, furthermore on the basis of the said estimated size of the drops of liquid water detected.

Thus, the system is capable of grading the risk of icing with improved precision.

For example, the size of a detected liquid water drop is estimated on the basis of the signal-to-noise ratio and of the distance of transit of the particle with respect to the focal point, this being deduced from the observed duration and the observed variation of frequency. This information affords access to a lower bound on the size of the particle via an assumption regarding its chemical composition.

In one embodiment, the said determining means are adapted for determining the severity of the icing, furthermore on the basis of the said measured temperature.

Thus, the system is capable of grading the risk of icing with improved precision.

According to one embodiment, the system furthermore comprises means for counting the total number of detected particles, in which the determining module is adapted for determining the severity of the icing furthermore on the basis of the total number of detected particles and of the number of detected drops of liquid water, for example on the basis of a ratio of these two numbers.

Thus, precision is improved.

In one embodiment, the system furthermore comprises a module for estimating the total mass of the particles detected on the basis of the total number of detected particles, and a module for estimating the liquid water mass detected on the basis of the number of drops of liquid water or spherical particles detected. The said determining module is adapted for determining the severity of the icing, furthermore on the basis of the total mass of detected particles and of the detected liquid water mass, for example on the basis of a ratio of these two masses.

Thus precision is improved.

According to one aspect of the invention, there is also proposed an aircraft equipped with a system such as described above.

According to one embodiment, the aircraft comprising, in addition to the laser anemometer measurement pathway including the said laser anemometry probe, two pathways for anemobarometric measurement, and means for managing the said pathways, adapted for increasing the weighting with which the information transmitted by the said pathway including the said laser anemometry probe is taken into account with respect to the information transmitted by the other two pathways for anemobarometric measurement, when icing conditions are detected by the said means for determining icing conditions.

Thus, it is possible to be able to limit or cancel the influence of the measurements of the pathways for anemobarometric measurement, when the laser anemometer measurement pathway including the said laser anemometry probe detects icing conditions to which the pathways for anemobarometric measurement are much more sensitive. Hence, the operating safety of the aircraft is greatly improved.

According to another aspect of the invention, there is also proposed a method of laser anemometry by probe employing continuous coherent detection, with single-particle mode, in which:

measurement signals of the said probe are analysed;
the temperature is measured;
and furthermore:
a first discrepancy, over a duration of observation of the said measurement signals, between the phase of the signal measured by the said probe and an expected phase, estimated on the basis of values of parameters characteristic of the laser beam emitted by the said probe, corresponding to the transit of a spherical particle, is compared with a first threshold of phase discrepancy;
a second discrepancy, over the said duration of observation of the said measurement signals, between the amplitude of the signal measured by the said probe and an expected amplitude, estimated as a function of values of parameters characteristic of the laser beam emitted by the said probe, corresponding to the transit of a spherical particle, is compared with a second threshold of amplitude discrepancy;
the said temperature is compared with a third threshold of temperature;
the presence of a liquid water drop is detected when the said first discrepancy is below the said first threshold and the said second discrepancy is below the said second threshold; and
icing conditions are determined when the said detection of the presence of a liquid water drop detect the presence of a liquid water drop, and when the said temperature is below the said third threshold.

The invention will be better understood on studying a few embodiments described by way of wholly non-limiting examples and illustrated by the appended drawings in which:

DETAILED DESCRIPTION OF THE INVENTION

In all the figures, elements having the same references are similar.

Figure 1:
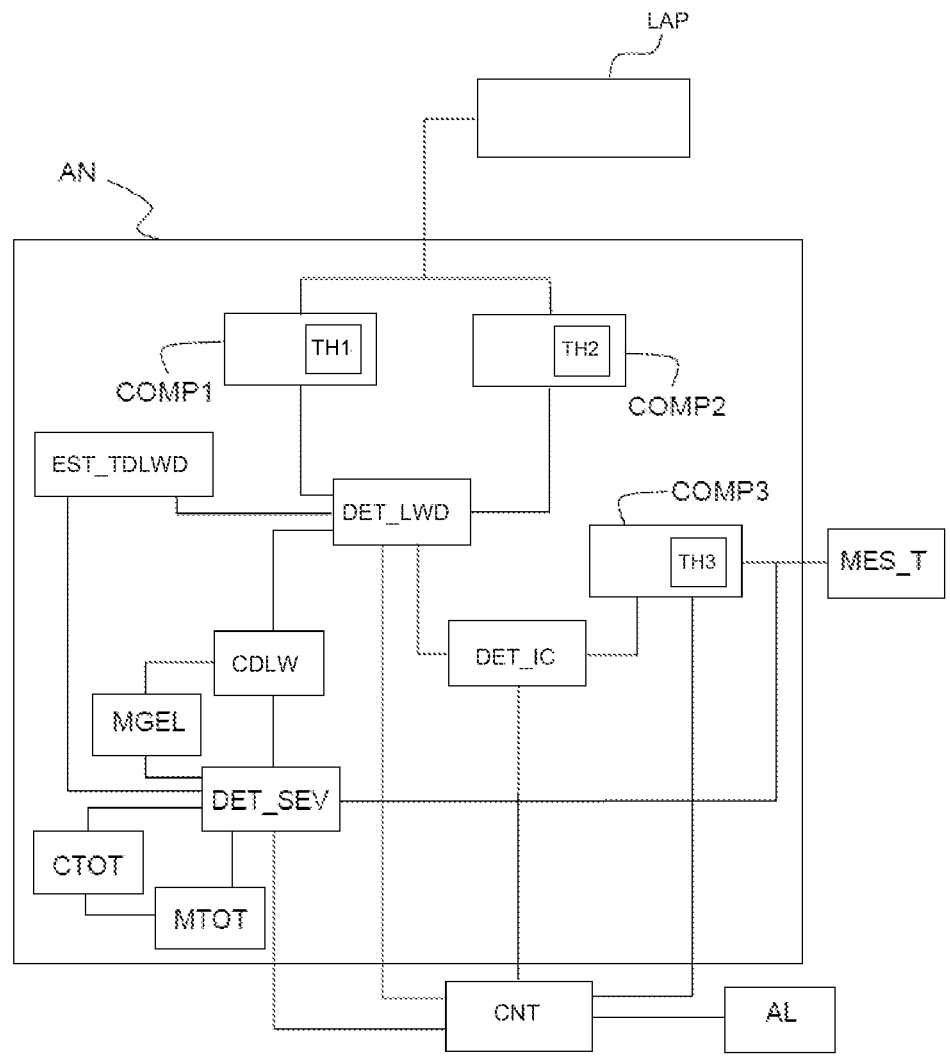
FIG. 1 illustrates a laser anemometry probe system employing continuous coherent detection, with single-particle mode, capable of detecting a risk of icing, and optionally of determining the severity of icing, according to one aspect of the invention.

As illustrated in FIG. 1, a laser anemometry probe LAP system employing continuous coherent detection, with single-particle mode, comprises means AN for analysing the measurement signals of the said laser anemometry probe LAP, and a sensor MES_T for measuring the temperature T. The system also comprises a first comparator COMP1 of a first discrepancy, over a duration of observation of the measurement signals, between the phase of the signal measured by the probe LAP and an expected phase, estimated on the basis of values of parameters characteristic of the laser beam emitted by the probe LAP, corresponding to the transit of a spherical particle, with a first threshold S1 of phase variation. Furthermore, the system comprises a second comparator COMP2, of a second discrepancy, over the duration of observation of the measurement signals, between the amplitude of the signal measured by the probe LAP and an expected amplitude, estimated as a function of values of parameters characteristic of the laser beam emitted by the probe LAP, corresponding to the transit of a spherical particle, with a second threshold S2 of amplitude variation.

A third comparator COMP3 makes it possible to compare the temperature T measured with a third threshold S3 of temperature, and a module DET_GEL for detecting the presence of a liquid water drop when the first discrepancy is below the first threshold S1 and the second discrepancy is below the second threshold S2. The system also comprises a module DET_CG for determining icing conditions when the module DET_GEL for detecting the presence of a liquid water drop detects the presence of a liquid water drop, and when the temperature T is below the third threshold S3.

For example, the laser anemometry probe LAP delivers a beam with circular polarization, so as to preserve optimal sensitivity, independently of the depolarizing properties of the target (particle) and of the propagation medium.

The duration of observation of the measurement signals is at least three times greater than the duration corresponding to the transit of a spherical particle across the laser beam.

For example, the first threshold S1 of phase variation lies between 0.1 and 1 radians, for example 0.2 radians, to take account of the measurement noise, and the second threshold S2 of amplitude variation is less than 20% of the said expected amplitude. The third threshold S3 of temperature lies between 5° C. and 15° C., and for example 10° C.

The system for detecting risk of icing SDG can also comprise, as represented in the example of FIG. 1, an alerting module AL for forewarning of a risk of icing, adapted so as to be activated by a control module CMD when the determining module DET_CG detects icing conditions.

The control module CMD may be adapted for monitoring the evolution of the temperature T after detection of presence of drops of liquid water. As a variant, or in combination, the control module CMD may be adapted for monitoring the detection of presence of drops of liquid water after measurement of the temperature T below the third threshold S3.

The system can comprise, furthermore, a module CGEL for counting the detected drops of liquid water, a module CTOT for counting the total number of detected particles, a module EST_MTOT for estimating the total mass of the particles detected on the basis of the total number of detected particles, and a module EST_MGEL for estimating the liquid water mass detected on the basis of the number of drops of liquid water or spherical particles detected.

The module EST_MGEL for estimating the liquid water mass detected, or LWC for "liquid water content", can perform its estimation on the basis of the number of drops of liquid water or spherical particles detected by the module CGEL for counting the detected drops of liquid water and the density of the liquid water.

The module EST_MTOT for estimating the total mass of the detected particles, or TWC for "total water content", can perform its estimation on the basis of the total number of particles detected by the module CTOT for counting the total number of detected particles, and the densities of the liquid water and of the solid water (ice).

For example, the two modules for estimating mass EST_MGEL and EST_MTOT can perform their respective estimations on the basis of the size or of an equivalent radius r of a particle, by calculating the mass of a particle by means of the following formula:

$$\frac{4}{3} \cdot \pi \cdot r^3 \cdot Coeff$$

in which Coeff is a calibration coefficient which takes account of the density and of optional other adjustment parameters related to the measurement system. The coefficient Coeff can optionally be different between a liquid particle and a solid particle, thus taking account of a density difference and of optional other differences.

The system also comprises means DET_SEV for determining the severity of the icing on the basis of the counting of the drops of liquid water detected per second, and/or on the basis of the size estimated by a module EST_TGELD for estimating the detected drops of liquid water, and/or the said measured temperature.

Furthermore, the determining module DET_SEV may be adapted for determining the severity of the icing furthermore on the basis of the total number of detected particles and of the number of drops of liquid water or spherical particles detected, and/or on the basis of the total mass of detected particles and of the detected liquid water mass. For example, the determining module DET_SEV can take account of a ratio of these two numbers or of these two masses, or of relative percentages in terms of number or mass of particles of liquid water and of particles of water (liquid and solid).

Such a system is particularly well suited to an aircraft such as an aeroplane or a helicopter. In this instance the alerting module AL forewarns the pilot of a risk of icing, and the pilot can then apply a procedure provided for this case. The alerting module AL can, for example, be embodied in the form of a man-machine interface, or in the form of an auditory alert.

Figure 2:
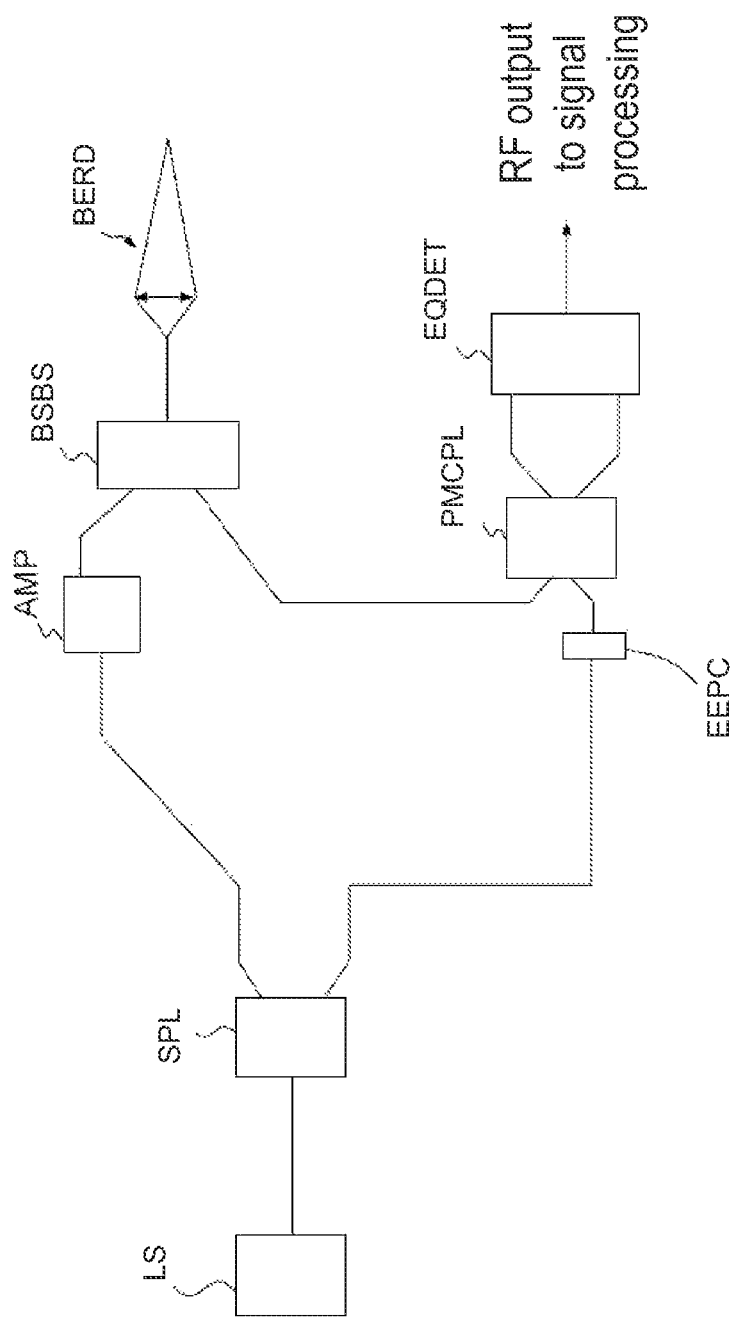
FIG. 2 illustrates an exemplary laser anemometry probe of FIG. 1.

FIG. 2 illustrates an exemplary laser anemometry probe LAP. This type of probe relies on a technique consisting in measuring the frequency shift, representative of the relative speed with respect to the air, between a laser beam emitted in the atmosphere and the beam backscattered by the natural aerosols of the air, used as wind field plotters. One speaks of longitudinal Doppler laser anemometry since the frequency shift which results from the Doppler effect is directly proportional to the projection of the speed vector onto the line of sight.

The useful information, carried by the Doppler frequency shift, is obtained by pericing a detection of coherent type; a beam arising from a coherent light source, for example a laser, is split into two beams. A first beam called the signal beam is dispatched into the measurement zone and a second beam called the reference beam or local oscillator constitutes a reference for the detection of the Doppler frequency shift.

As illustrated in FIG. 2, the laser anemometry probe LAP comprises a laser source SL providing a linearly polarized reference wave, a splitter SEP splitting the signal originating from the laser source SL into a signal transmitted towards an amplifier AMP and a signal transmitted towards a polarization-maintaining coupler CPLMP. The laser anemometry probe LAP also comprises a beam emitter/receiver device DERF along the direction of the axis of the probe, as well as a backscattered beam splitter SFRD disposed between the amplifier AMP and the emitter/receiver device DERF and transmitting the signal originating from the amplifier AMP towards the emitter/receiver device DERF. The signal backscattered by the emitter/receiver device DERF is transmitted by the backscattered beam splitter SFRD towards the polarization-maintaining coupler CPLMP. The single-axis laser anemometry probe comprises, furthermore, an element for effecting polarization coherence EMCP disposed upstream of the polarization-maintaining coupler CPLMP so as to ensure that the backscattered signal and the reference wave possess the same polarization on input to the polarization-maintaining coupler CPLMP, and an equilibrated detector DETEQ disposed downstream of the polarization-maintaining coupler CPLMP. The polarization-maintaining coupler CPLMP provides on each output pathway half the backscattered signal and half the reference wave. The two output signals of the polarization-maintaining coupler are transmitted to the equilibrated detector DETEQ, which, for example, comprises two diodes, and delivers as output the difference of the signals provided by the two diodes. The portion of each signal changing channel in the polarization-maintaining coupler CPLMP undergoes a phase delay and the beat produced during detection on the two diodes of the equilibrated detector DETEQ are in phase opposition. The differential output therefore makes it possible to add up the signal powers received. The output signal of the equilibrated detector DETEQ is thereafter transmitted to an electronic control unit, not represented, so as to be processed.

The icing phenomenon is due mainly to the presence of liquid water at negative temperature, or, stated otherwise, to the presence of supercooled water. This water freezes instantaneously in contact with an element or a probe.

The water droplets are of relatively considerable size, generally greater than 50 μm in diameter, thereby making it possible to detect them with laser anemometry probe LAP using a relatively wide and divergent beam, in fact outside of the focusing point where the small particles used for speed measurement are detected, of the order of 100 nm in diameter.

The anemometric measurement is performed at the beam focusing point, situated some fifty or so centimeters from the laser anemometry probe LAP. The measurement volume resembles an ellipsoid, with a maximum width of the order of 100 μm and of the order of 1 cm in length.

The signal originates from particles situated beyond the focusing point, a zone in which the detection sensitivity decreases rapidly, on account of the divergence of the beam. Nonetheless, since the water droplets responsible for the icing phenomenon are of large dimension, of the order of 10 to 100 μm, they may be visible, and may be so for a considerable duration, of the order of 10 to 100 μs, the diameter of the beam being considerable, of the order of 1 cm.

Figure 3A:
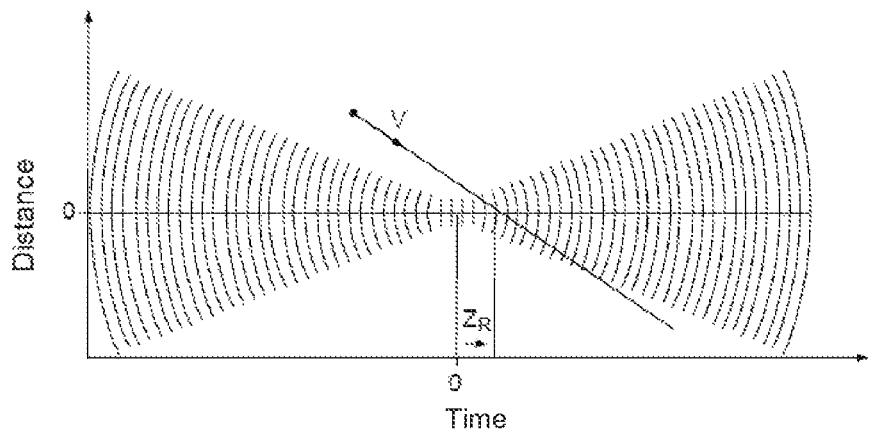
FIGS. 3a, 3b and 3c illustrate a measurement by the laser anemometry probe, according to one aspect of the invention.
Figure 3B:
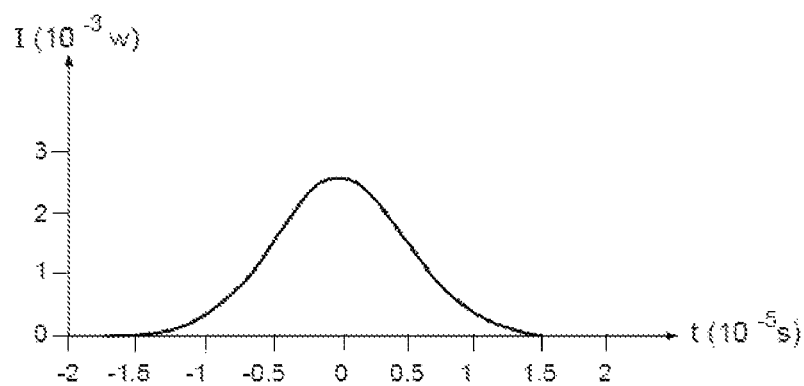
Figure 3C:
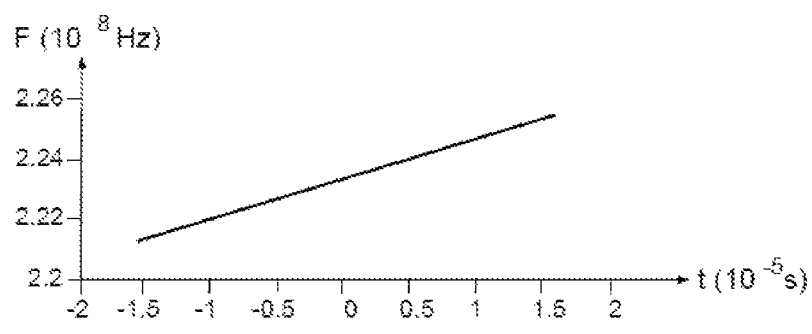

As illustrated in FIGS. 3a, 3b and 3c, when a particle cuts the beam emitted by the laser anemometry probe LAP, the electrical signal obtained as output from the laser anemometry probe LAP is a pulse or "burst", the electric current being proportional to the square root of the optical power of the backscattered signal.

FIGS. 3a, 3b and 3c are given by way of illustration, to understand the shape of the signals. In this instance if the radius of the beam at the focusing point or "waist" at $1/e^2$ (e being the exponential number) equals 50 μm, with a particle speed with respect to the beam equal to 200 m/s and an angle of 60° between the axis of the beam and the speed vector, we obtain a longitudinal speed of 100 m/s i.e. a Doppler frequency of about 130 MHz, and a transverse speed of about 173 m/s, for a pulse duration of 580 ns. $Z_R$ corresponds to the Rayleigh distance which is characteristic since at a distance of $Z_R$ from the focusing point, the wavefronts exhibit their maximum curvature. The frequency variation over the duration of the pulse is then a maximum. $Z_R$ equals about 5 mm for a radius of the beam at the focusing point or waist equal to 50 μm and a wavelength of 1.5 μm.

FIG. 3b represents a Gaussian envelope corresponding to the illumination profile (Gaussian beam), i.e. to the intensity I as a function of time t. The intensity I corresponds strictly to the optical power, in W, received for a particle of unit cross-section cutting the beam at $Z_0=-0.20$ m, at a speed of 200 m/s and an angle of 45° with respect to the beam, for an emitted laser power of 1 W, with a radius of the beam at the focusing point or "waist" of 50 μm.

FIG. 3c illustrates the modulation of the frequency observed on account of the curvature of the wavefront, for a particle cutting the beam at $Z_0=-0.20$ m, the beam being characterized by a radius of the beam at the focusing point or waist equal to 50 μm.

Such a system makes it possible to detect risk of icing is particularly well suited to be embedded aboard an aircraft.

Furthermore, if the aircraft comprises, in addition to the laser anemometer measurement pathway including the said laser anemometry probe, two pathways for anemobarometric measurement, and a module for managing the said pathways adapted for increasing the weighting with which the information transmitted by the pathway including the laser anemometry probe LAP is taken into account with respect to the information transmitted by the other two pathways for anemobarometric measurement, when a risk of icing is detected.

The invention claimed is:

1. Laser anemometry probe (LAP) system employing continuous coherent detection, with single-particle mode, comprising:
   means (AN) for analyzing measurement signals of the said probe (LAP);
   means (MES_T) for measuring a temperature (T);
   characterized in that the LAP system comprises, furthermore:
   first means (COMP1) for comparing a first discrepancy, over a duration of observation of the said measurement signals, between the phase of the signal measured by the said probe (LAP) and an expected phase, the expected phase being estimated on the basis of values of parameters characteristic of a laser beam emitted by the said probe, corresponding to the transit of a spherical particle, with a first threshold (S1) of phase discrepancy;
   second means (COMP2) for comparing a second discrepancy, over the said duration of observation of the said measurement signals, between the amplitude of the signal measured by the said probe (LAP) and an expected amplitude, the expected amplitude being estimated as a function of values of parameters characteristic of the laser beam emitted by the said probe, corresponding to the transit of said spherical particle, with a second threshold (S2) of amplitude discrepancy;
   third means (COMP3) for comparing the said temperature (T) with a third threshold (S3) of temperature;
   means (DET_GEL) for detecting the presence of a liquid water drop when the said first discrepancy is below the said first threshold (S1) and the said second discrepancy is below the said second threshold (S2); and
   means (DET_CG) for determining icing conditions when the said means (DET_GEL) for detecting the presence of a liquid water drop detect the presence of a liquid water drop, and when the said temperature (T) is below the said third threshold (S3).

2. System according to claim 1, in which the said laser anemometry probe (LAP) delivers a beam with circular polarization.

3. System according to claim 1, in which the said first threshold (S1) of phase discrepancy lies between 0.1 and 1 radian, to take account of measurement noise.

4. System according to claim 1, in which the said second threshold (S2) of amplitude discrepancy is less than 20% of the said expected amplitude.

5. System according to claim 1, in which the said third threshold (S3) of temperature lies between 5° C. and 15° C.

6. System according to claim 5, in which the said third threshold (S3) of temperature equals substantially 10° C.

7. System according to claim 1, comprising alerting means (AL) for forewarning of a risk of icing, adapted so as to be activated by control means (CMD) when the said determining means (DET_CG) detect icing conditions.

8. System according to claim 7, in which the said control means (CMD) are adapted for monitoring the evolution of the said temperature (T) after detecting the presence of drops of liquid water.

9. System according to claim 7, in which the said control means (CMD) are adapted for monitoring the detection of the presence of drops of liquid water after measurement of the said temperature (T) below the said third threshold (S3).

10. System according to claim 1, comprising, furthermore, means (CGEL) for counting the detected drops of liquid water, and means (DET_SEV) for determining the severity of the icing on the basis of the said counting of the drops of liquid water detected per second.

11. System according to claim 10, comprising, furthermore, means for estimating the size of a detected liquid water drop (EST_TGELD), in which the said determining means (DET_SEV) are adapted for determining the severity of the icing, furthermore on the basis of the said estimated size of the drops of liquid water detected.

12. System according to claim 10, in which the said determining means (DET_SEV) are adapted for determining the severity of the icing, furthermore on the basis of the said measured temperature (T).

13. System according to claim 12, comprising, furthermore, means (CTOT) for counting the total number of detected particles, in which the said determining means (DET_SEV) are adapted for determining the severity of the icing, furthermore on the basis of the total number of detected particles and of the number of drops of liquid water or spherical particles detected.

14. System according to claim 13, further comprising means (EST_MTOT) for estimating the total mass of the particles detected on the basis of the total number of detected particles, and means (EST_MGEL) for estimating the liquid water mass detected on the basis of the number of drops of liquid water or spherical particles detected, in which the said determining means (DET_SEV) are adapted for determining the severity of the icing, furthermore on the basis of the total mass of detected particles and of the detected liquid water mass.

15. Aircraft equipped with a laser anemometry probe (LAP) system employing continuous coherent detection, with single-particle mode, comprising:
   means (AN) for analysing the measurement signals of the said probe (LAP);
   means (MES_T) for measuring a temperature (T);

characterized in that the LAP comprises, furthermore:
- first means (COMP1) for comparing a first discrepancy, over a duration of observation of the said measurement signals, between the phase of the signal measured by the said probe (LAP) and an expected phase, the expected phase being estimated on the basis of values of parameters characteristic of the laser beam emitted by the said probe, corresponding to the transit of a spherical particle, with a first threshold (S1) of phase discrepancy;
- second means (COMP2) for comparing a second discrepancy, over the said duration of observation of the said measurement signals, between the amplitude of the signal measured by the said probe (LAP) and an expected amplitude, the expected amplitude being estimated as a function of values of parameters characteristic of a laser beam emitted by the said probe, corresponding to the transit of said spherical particle, with a second threshold (S2) of amplitude discrepancy;
- third means (COMP3) for comparing the said temperature (T) with a third threshold (S3) of temperature;
- means (DET_GEL) for detecting the presence of a liquid water drop when the said first discrepancy is below the said first threshold (S1) and the said second discrepancy is below the said second threshold (S2); and
- means (DET_CG) for determining icing conditions when the said means (DET_GEL) for detecting the presence of a liquid water drop detect the presence of a liquid water drop, and when the said temperature (T) is below the said third threshold (S3).

16. Aircraft according to claim 15, comprising, in addition to the laser anemometer measurement pathway including the said laser anemometry probe (LAP), two pathways for anemobarometric measurement, and means for managing the said pathways, adapted for increasing the weighting with which the information transmitted by the said pathway including the said laser anemometry probe is taken into account with respect to the information transmitted by the other two pathways for anemobarometric measurement, when icing conditions are detected by the said means (DET_CG) for determining icing conditions.

17. Method of laser anemometry by probe (LAP) employing continuous coherent detection, with single-particle mode, in which:
- measurement signals of the said probe (LAP) are analysed;
- the temperature (T) is measured;

characterized in that:
- a first discrepancy, over a duration of observation of the said measurement signals, between the phase of the signal measured by the said probe (LAP) and an expected phase, the expected phase being estimated on the basis of values of parameters characteristic of the laser beam emitted by the said probe, corresponding to the transit of a spherical particle, is compared with a first threshold (S1) of phase discrepancy;
- a second discrepancy, over the said duration of observation of the said measurement signals, between the amplitude of the signal measured by the said probe (LAP) and an expected amplitude, the expected amplitude being estimated as a function of values of parameters characteristic of a laser beam emitted by the said probe, corresponding to the transit of said spherical particle, is compared with a second threshold (S2) of amplitude discrepancy;
- the said temperature (T) is compared with a third threshold (S3) of temperature;
- the presence of a liquid water drop is detected when the said first discrepancy is below the said first threshold (S1) and the said second discrepancy is below the said second threshold (S2); and
- icing conditions are determined when the said detection of the presence of a liquid water drop detect the presence of a liquid water drop, and when the said temperature (T) is below the said third threshold (S3).

* * * * *